United States Patent
Sloan et al.

(10) Patent No.: US 11,737,687 B2
(45) Date of Patent: Aug. 29, 2023

(54) OPTIMIZING MEDICATION DOSAGE BASED ON ANALYTE SENSOR DATA

(71) Applicant: Abbott Diabetes Care Inc., Alameda, CA (US)

(72) Inventors: Mark K. Sloan, Redwood City, CA (US); Martin J. Fennell, Concord, CA (US); Daniel M. Bernstein, El Granada, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 176 days.

(21) Appl. No.: 16/252,980

(22) Filed: Jan. 21, 2019

(65) Prior Publication Data
US 2019/0150808 A1 May 23, 2019

Related U.S. Application Data

(63) Continuation of application No. 14/633,090, filed on Feb. 26, 2015, now Pat. No. 10,194,841, which is a
(Continued)

(51) Int. Cl.
*A61B 5/145* (2006.01)
*A61M 5/172* (2006.01)
(Continued)

(52) U.S. Cl.
CPC ........ *A61B 5/14532* (2013.01); *A61B 5/4839* (2013.01); *A61M 5/1723* (2013.01);
(Continued)

(58) Field of Classification Search
CPC ........ A61M 5/1723; A61M 2005/1726; A61M 2005/14208; A61B 5/14532; A61B 5/4839; G16H 20/10; G16H 20/17
See application file for complete search history.

(56) References Cited

U.S. PATENT DOCUMENTS 5,569,186 A 10/1996 Lord et al.
5,665,065 A 9/1997 Colman et al.
(Continued)

FOREIGN PATENT DOCUMENTS

WO    WO 99/56613 A1    11/1999
WO    WO 2004/009161 A1    1/2004
(Continued)

OTHER PUBLICATIONS

WO PCT/US13/57143 ISR, Nov. 22, 2013.
(Continued)

*Primary Examiner* — Amber R Stiles
*Assistant Examiner* — Leah J Swanson
(74) *Attorney, Agent, or Firm* — Sterne, Kessler, Goldstein & Fox P.L.L.C.

(57) ABSTRACT

Methods, apparatuses, and systems are provided for determining whether to administer a medication dose as a single dose or whether to fractionate the single dose to be administered as at least two discrete doses. Embodiments include determining a first analyte level and a first rate of change of the analyte level; determining an initial medication dose based on one or more anticipated subsequent medication doses, the first analyte level relative to an analyte level threshold, and the first rate of change of the analyte level relative to a rate of change threshold; administering the initial medication dose; determining a second analyte level and a second rate of change of the analyte level based on subsequent analyte data; and determining a subsequent medication dose based on the second analyte level relative to the analyte level threshold and the second rate of change relative to the rate of change threshold.

21 Claims, 4 Drawing Sheets

Related U.S. Application Data continuation of application No. PCT/US2013/057143, filed on Aug. 28, 2013.

(60) Provisional application No. 61/695,152, filed on Aug. 30, 2012.

(51) Int. Cl.
*A61B 5/00* (2006.01)
*G16H 20/17* (2018.01)
*G16H 20/10* (2018.01)
*A61M 5/142* (2006.01)

(52) U.S. Cl.
CPC ............ *G16H 20/10* (2018.01); *G16H 20/17* (2018.01); *A61M 2005/14208* (2013.01)

(56) References Cited

U.S. PATENT DOCUMENTS

| | | | |
|---|---|---|---|
| 5,822,715 A * | 10/1998 | Worthington | A61B 5/411 702/19 |
| 6,175,752 B1 | 1/2001 | Say et al. | |
| 6,544,212 B2 | 4/2003 | Galley et al. | |
| 6,572,542 B1 | 6/2003 | Houben et al. | |
| 7,591,801 B2 | 9/2009 | Brauker et al. | |
| 8,060,318 B2 | 11/2011 | Vering et al. | |
| 2003/0114836 A1 | 6/2003 | Estes et al. | |
| 2005/0038332 A1 | 2/2005 | Saidara et al. | |
| 2005/0192557 A1 | 9/2005 | Brauker et al. | |
| 2006/0276771 A1 | 12/2006 | Galley et al. | |
| 2007/0106135 A1 | 5/2007 | Sloan et al. | |
| 2007/0149874 A1 | 6/2007 | Say et al. | |
| 2007/0179370 A1 | 8/2007 | Say et al. | |
| 2007/0208244 A1 | 9/2007 | Brauker et al. | |
| 2008/0119710 A1 | 5/2008 | Reggiardo et al. | |
| 2008/0235053 A1 | 9/2008 | Ray et al. | |
| 2008/0262469 A1 | 10/2008 | Brister et al. | |
| 2008/0275318 A1 | 11/2008 | Lastovich et al. | |
| 2008/0287761 A1 | 11/2008 | Hayter et al. | |
| 2008/0287762 A1 | 11/2008 | Hayter et al. | |
| 2008/0287763 A1 | 11/2008 | Hayter | |
| 2008/0288180 A1 | 11/2008 | Hayter et al. | |
| 2008/0312841 A1 | 12/2008 | Hayter | |
| 2008/0312842 A1 | 12/2008 | Hayter et al. | |
| 2008/0312844 A1 | 12/2008 | Hayter et al. | |
| 2008/0312845 A1 | 12/2008 | Hayter et al. | |
| 2009/0005665 A1 | 1/2009 | Hayter et al. | |
| 2009/0006034 A1 | 1/2009 | Hayter et al. | |
| 2009/0055149 A1 | 2/2009 | Hayter et al. | |
| 2009/0105636 A1 | 4/2009 | Hayter et al. | |
| 2009/0192366 A1 | 7/2009 | Mensinger et al. | |
| 2009/0192380 A1 | 7/2009 | Shariati et al. | |
| 2009/0192745 A1 | 7/2009 | Kamath et al. | |
| 2009/0192751 A1 | 7/2009 | Kamath et al. | |
| 2009/0216102 A1 | 8/2009 | Say et al. | |
| 2009/0221890 A1 | 9/2009 | Saffer et al. | |
| 2010/0057057 A1 | 3/2010 | Hayter et al. | |
| 2010/0161236 A1 | 6/2010 | Cohen et al. | |
| 2010/0174266 A1 * | 7/2010 | Estes | A61M 5/14244 604/504 |
| 2010/0185142 A1 | 7/2010 | Kamen et al. | |
| 2010/0185175 A1 | 7/2010 | Kamen et al. | |
| 2010/0191472 A1 | 7/2010 | Doniger et al. | |
| 2010/0198142 A1 | 8/2010 | Sloan et al. | |
| 2010/0198314 A1 | 8/2010 | Wei | |
| 2010/0295686 A1 * | 11/2010 | Sloan | G08B 21/0453 340/573.1 |
| 2011/0077494 A1 | 3/2011 | Doniger et al. | |
| 2014/0024907 A1 | 1/2014 | Howell et al. | |
| 2015/0217055 A1 | 8/2015 | Booth et al. | |

FOREIGN PATENT DOCUMENTS

| | | | |
|---|---|---|---|
| WO | WO 2008/030347 A2 | 3/2008 | |
| WO | WO 2009/146119 A2 | 12/2009 | |
| WO | WO 2010/091129 A1 | 8/2010 | |
| WO | WO 2011/041007 A1 | 4/2011 | |
| WO | WO 2011/060923 A2 | 5/2011 | |

OTHER PUBLICATIONS

Cunningham, David D. and Stenken, Julia A., Editors, "In Vivo Glucose Sensing," Chemical Analysis, vol. 174, John Wiley & Sons, Inc., Hoboken, NJ 2010; 27 pages.

PMA Approvals FDA—webpage available at: https://www.fda.gov; 3 pages, accessed Sep. 14, 2022.

PMA database search for Freestyle Navigator Continuous Glucose Monitor-https://www.fda.gov; 6 pages, accessed Sep. 14, 2022.

Getting Started with CareLink Personal Software Continuous Glucose Monitoring; Medtronic, 2009, 28 pages.

Sparacino, Giovanni et al., "Glucose Concentration can be Predicted Ahead in Time From Continuous Glucose Monitoring Sensor Time-Series," IEEE Transactions on Biomedical Engineering, vol. 54, No. 5, May 2007; 7 pages.

Sandham, William et al., "Blood Glucose Prediction for Diabetes Therapy Using a Recurrent Artificial Neural Network," 9th European Signal Processing Conference (EUSIPCO 1998), 1998, pp. 1-4.

FreeStyle Navigator Continuous Glucose Monitoring System, User's Guide, Abbott Diabetes Care Inc., May 2008; 195 pages.

Exhibit CP-3, Expert Report of Dr. Cesar C. Palerm, Sep. 20, 2022: "In Vivo Glucose Sensing, Chemical Analysis, A Series of Monographs on Analytical Chemistry and Its Applications," vol. 174, Wiley (2010) Chp. 5, pp. 143-147.

Exhibit CP-4, Expert Report of Dr. Cesar C. Palerm, Sep. 20, 2022, "Animas® VibeTM, the First Integrated Offering from Animas Corporation and Dexcom, Inc, Receives European CE Mark Approval", Products & Operating Company, 2011, 4 pages.

Exhibit CP-6, Second Expert Report of Dr. Cesar C. Palerm, Oct. 21, 2022, Bailey, T.S. et al., "Reduction in Hemoglobin A1c with Real-Time Continuous Glucose Monitoring: Results from a 12-Week Observational Study" Diabetes Technology & Therapeutics, 2007, 9(3):203-210.

Exhibit CP-7, Second Expert Report of Dr. Cesar C. Palerm, Oct. 21, 2022, Garg, S. et al., "Improvement in Glycemic Excursions with a Transcutaneous, Real-Time Continuous Glucose Sensor", Diabetes Care, 2006, 29(12):44-50.

Exhibit CP-8, Second Expert Report of Dr. Cesar C. Palerm, Oct. 21, 2022, Garg, S. et al, "Relationship of Fasting and Hourly Blood Glucose Levels to HbA1c Values", Diabetes Care, 2006, 6(12):2644-2649.

Exhibit CP-10, Second Expert Report of Dr. Cesar C. Palerm, Oct. 21, 2022, "Standards of Medical Care in Diabetes-2009" Position Statement, American Diabetes Association, 2009, Diabetes Care, 32(1):513-561.

Exhibit No. 2, to the Expert Report of Professor Nick Oliver, Sep. 20, 2022, "Note for Guidance on Clinical Investigation of Medicinal Products in the Treatment of Diabetes Mellitus," the European Agency for the Evaluation of Medicinal Products, 2002, 12 pages.

Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.

Exhibit No. 4, to the Expert Report of Professor Nick Oliver, Sep. 20, 2022, Amiel, S. A., et al., "Hypoglycaemia in Type 2 diabetes", Diabetic Medicine, 2008, 25:245-254.

Exhibit No. 5, to the Expert Report of Professor Nick Oliver, Sep. 20, 2022, Swinnen, S.G.H.A. et al., "Changing the glucose cut-off values that define Hypoglycaemia has a major effect on reported frequencies of hypoglycaemia", Diabetologia, 2009, 52:38-41.

Exhibit No. 6, to the Expert Report of Professor Nick Oliver, Sep. 20, 2022, Frier, B.M. "Defining hypoglycaemia: what level has clinical relevance?", Diabetologia, 2009, 52:31-34.

Exhibit No. 7, to the Expert Report of Professor Nick Oliver, Sep. 20, 2022, Cryer, P.E. "Preventing Hypoglycaemia: what is the appropriate glucose alert value?" Diabetologia, 2009, 53:35-37.

(56) References Cited

OTHER PUBLICATIONS

Exhibit No. 8, to the Expert Report of Professor Nick Oliver, Sep. 20, 2022, Choudhary, P. et al., "Hypoglycaemia in the treatment of diabetes mellitus" Oxford Textbook of Endocrinology and Diabetes, 2011 pp. 1849-1860.

Exhibit No. 9, to the Expert Report of Professor Nick Oliver, Sep. 20, 2022, "Guideline on clinical investigation of medicinal products in the treatment or prevention of diabetes mellitus" European Medicines Agency, May 14, 2012, 28 pages.

Exhibit No. 11, to the Expert Report of Professor Nick Oliver, Sep. 20, 2022, "The Effect of Intensive Treatment of Diabetes on the Development and Progression of Long-Term Complications in Insulin-Dependent Diabetes Mellitus" The New England Journal of Medicine, 1993, 329(14):977-986.

Exhibit No. 12, to the Expert Report of Professor Nick Oliver, Sep. 20, 2022, National Service Framework for Diabetes: Standards, Dept. of Health, 2002, 48 pages.

Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.

Exhibit No. 14, to the Expert Report of Professor Nick Oliver, Sep. 20, 2022, "Type 1 diabetes: diagnosis and management of type 1 diabetes in children, young people and adults" National Institute for Clinical Excellence, Clinical Guideline 15, Jul. 2004, 113 pages.

Exhibit No. 15, to the Expert Report of Professor Nick Oliver, Sep. 20, 2022, Pickup, John C. "Glucose monitoring", Oxford Textbook of Endocrinology and Diabetes, 2011, pp. 1861-1869.

Exhibit No. 16, to the Expert Report of Professor Nick Oliver, Sep. 20, 2022, Pickup, J.C. et al., "Glycaemic control in type 1 diabetes during real time continuous glucose monitoring compared with self monitoring of blood glucose: meta-analysis of randomised controlled trials using individual patient data" BMJ, 2011; 14 pages.

Exhibit No. 17, to the Expert Report of Professor Nick Oliver, Sep. 20, 2022, "Diabetes (type 1), PSP Top 10", James, Lind Alliance, Priority Setting Partnerships, 2011, 4 pages.

Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.

Exhibit No. 21, to the Expert Report of Professor Nick Oliver, Sep. 20, 2022, DeVries, J.H. "Glucose Sensing Issues for the Artificial Pancreas" Journal of Diabetes Science and Technology, 2008, 2(4):732-734.

Exhibit No. 23, to the Expert Report of Professor Nick Oliver, Sep. 20, 2022, Internet Archive, WayBack Machine, Medtronic MiniMed, 2004, 20 pages.

Exhibit No. 24, to the Expert Report of Professor Nick Oliver, Sep. 20, 2022, "Glucowatch G2, Automatic Glucose Biographer and Autosensors," 2002, 70 pages.

Exhibit No. 25, to the Expert Report of Professor Nick Oliver, Sep. 20, 2022, "Guardian® Real-Time Continuous Glucose Monitoring System, User Guide," Medtronic MiniMed, 2006, 181 pages.

Exhibit No. 26, to the Expert Report of Professor Nick Oliver, Sep. 20, 2022, "CGMS® iProTM Continuous Glucose Recorder, User Guide," Medtronic MiniMed, 2007, 36 pages.

Exhibit No. 27, to the Expert Report of Professor Nick Oliver, Sep. 20, 2022, "FreeStyle Navigator Continuous Glucose Monitoring System, User Guide," Abbott, 2008, 2010, 135 pages.

Exhibit No. 30, to the Expert Report of Professor Nick Oliver, Sep. 20, 2022, Revised specification for publication No. US2007208244A1, 2007, 170 pages.

Exhibit No. 31, to the Expert Report of Professor Nick Oliver, Sep. 20, 2022, Revised Specification for EP625, 2008, 30 pages.

Exhibit No. 32, to the Expert Report of Professor Nick Oliver, Sep. 20, 2022, Puhr, S. et al., "Real-World Hypoglycemia Avoidance with a Predictive Low Glucose Alert Does Not Depend on Frequent Screen Views", Journal of Diabetes Sciences and Technology, 2004, 14(1): 83-86.

Exhibit No. 37, to the Second Expert Report of Professor Nick Oliver, Oct. 21, 2022, Oliver, N.S., et al., "Glucose sensors: a review of current and emerging technology", Diabetic Medicine, 2009, 26:197-210.

"Dexcom's 7-Day Continuous Glucose Monitoring System," Jun. 1, 2007, https://newatlas.com/; 1 page.

\* cited by examiner

OPTIMIZING MEDICATION DOSAGE BASED ON ANALYTE SENSOR DATA

PRIORITY

This application is a continuation of U.S. patent application Ser. No. 14/633,090, filed Feb. 26, 2015, granted as U.S. Pat. No. 10,194,841, which application is a continuation of International Application No. PCT/US2013/057143, filed on Aug. 28, 2013, which claims priority to U.S. Provisional Patent Application Ser. No. 61/695,152, filed on Aug. 30, 2012, all of which applications are incorporated by reference herein in their entirety for all purposes.

BACKGROUND

The detection of the level of glucose or other analytes, such as lactate, oxygen or the like, in certain individuals is vitally important to their health. For example, the monitoring of glucose is particularly important to individuals with diabetes. People with diabetes may need to monitor glucose levels to determine when insulin is needed to reduce glucose levels in their bodies or when additional glucose is needed to raise the level of glucose in their bodies.

Devices have been developed for continuous and automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

SUMMARY

Embodiments of the present disclosure include computer-implemented methods and processor-based systems that determine whether to administer a medication dose as a single dose or whether to fractionate the single dose and administer it as two or more discrete doses. The embodiments of the present disclosure include receiving analyte data related to an analyte level from an in vivo analyte sensor positioned through a skin layer. The in vivo sensor may be in contact with an interstitial fluid or blood. An analyte level and a rate of change of the analyte level are determined based on the received analyte data. A determination is made whether medication is required based on a comparison of the determined analyte level to a predetermined analyte level threshold and a comparison of the determined rate of change of the analyte level to a predetermined rate level. The option to administer the medication in two or more doses is also considered. The medication dose to be administered is calculated along with a prediction of whether if the calculated medication dose is administered as one dose, a hypoglycemic event may occur. The prediction includes variability and safety margin. Based on the prediction, the calculated medication dose may be administered as at least two discrete medication doses at two different times.

In some embodiments, the present disclosure provides a method of optimizing medication dosage based on analyte sensor data. The method includes determining a first analyte level and a first rate of change of the analyte level based on analyte data received from an in vivo sensor; determining an initial medication dose based on one or more anticipated subsequent medication doses, the first analyte level relative to an analyte level threshold, and the first rate of change of the analyte level relative to a rate of change threshold; providing an indication to administer the initial medication dose; determining a second analyte level and a second rate of change of the analyte level based on subsequent analyte data received from the sensor; and determining a subsequent medication dose based on the second analyte level relative to the analyte level threshold and the second rate of change of the analyte level relative to the rate of change threshold.

In some other embodiments, the present disclosure provides an apparatus for optimizing medication dosage based on analyte sensor data. The apparatus includes a processor and a memory coupled to the processor. The memory is operative to store instructions executable by the processor. The instructions include determining a first analyte level and a first rate of change of the analyte level based on analyte data received from an in vivo sensor, determining an initial medication dose based on one or more anticipated subsequent medication doses, the first analyte level relative to an analyte level threshold, and the first rate of change of the analyte level relative to a rate of change threshold, providing an indication to administer the initial medication dose, determining a second analyte level and a second rate of change of the analyte level based on subsequent analyte data received from the sensor, and determining a subsequent medication dose based on the second analyte level relative to the analyte level threshold and the second rate of change of the analyte level relative to the rate of change threshold.

In yet other embodiments, the present disclosure provides a system for optimizing medication dosage based on analyte sensor data. The system includes an analyte sensor configured to be transcutaneously positioned through a skin layer and maintained in fluid contact with an interstitial fluid under the skin layer during a predetermined time period. The analyte sensor includes a proximal portion and a distal portion. The system also includes sensor electronics coupled to the analyte sensor. The sensor electronics includes a circuit board having a conductive layer and a sensor antenna disposed on the conductive layer; and one or more electrical contacts provided on the circuit board and coupled with the proximal portion of the analyte sensor to maintain electrical communication. The system also includes a receiver unit. The receiver unit includes a processor and a memory coupled to the processor. The memory is operative to store instructions executable by the processor. The instructions include determining a first analyte level and a first rate of change of the analyte level based on analyte data received from the analyte sensor, determining an initial medication dose based on one or more anticipated subsequent medication doses, the first analyte level relative to an analyte level threshold, and the first rate of change of the analyte level relative to a rate of change threshold, providing an indication to administer the initial medication dose, determining a second analyte level and a second rate of change of the analyte level based on subsequent analyte data received from the sensor, and determining a subsequent medication dose based on the second analyte level relative to the analyte level threshold and the second rate of change of the analyte level relative to the rate of change threshold.

Numerous other aspects and embodiments are provided. These other features and aspects of the present disclosure will become more fully apparent from the following detailed description, the appended claims, and the accompanying drawings.

DETAILED DESCRIPTION

Figure 1:
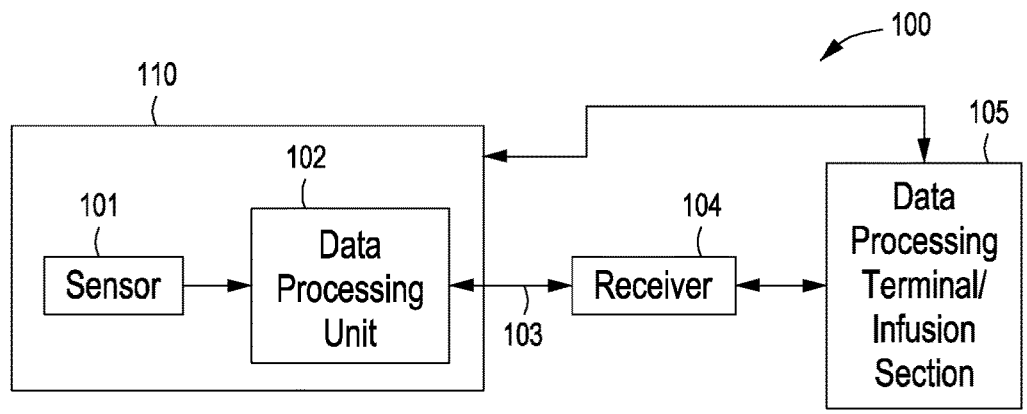
FIG. 1 depicts a data monitoring and management system such as, for example, an analyte (e.g., glucose) monitoring system in accordance with certain embodiments of the present disclosure.

The present disclosure relates to analyte monitoring systems and health management systems. More specifically, the present disclosure relates to methods, apparatus, and systems for optimizing the administration of a dose of medication. In some embodiments, the invention includes determining whether to administer a medication dose as a single dose or whether to fractionate the single dose to be administered as multiple discrete doses.

In continuous, semi-continuous or discrete analyte monitoring systems for insulin therapy, analyte levels of a patient are monitored and/or measured, and the measured analyte levels are used for treatment. For example, real time values of measured analyte levels of a patient allow for more robust and accurate diabetes treatment. Moreover, a profile of a series of measured analyte levels of a diabetic patient can provide valuable information regarding the fluctuations and variations of the analyte levels in a diabetic patient. In turn, this type of information would be invaluable in establishing a suitable insulin therapy regimen.

Many diabetic patients that use an infusion device such as an infusion pump generally have preset or pre-established basal profiles which are programmed or stored into the infusion device by the patient or the patient's physician. Indeed, based on several factors such as insulin sensitivity, the patient's physiology and other variable factors that affect the patient's analyte levels, the physician may tailor the basal profiles of the patient to be programmed into the infusion device such that the patient's analyte level is maintained within an acceptable range, and thus the patient is not going to experience hyperglycemia or hypoglycemia.

While physicians attempt to best determine the most suitable basal profiles for each diabetic patient using the infusion device, it is often difficult to attain the most suitable profiles to ensure the safe operating range of the infusion device while providing the patient with the most suitable level of insulin at all times when the patient is wearing and operating the infusion device. For example, to compensate for a predicted physiologically relevant drop in glucose due to a bolus dose being administered, some users may manually calculate fractionated bolus doses, based on a meal-time bolus, that are administered over different periods of time to help regulate blood glucose levels in a targeted range.

Often, diabetics who use infusion pumps run basal profiles to maintain a steady level of insulin and also supplement with additional bolus doses and/or temporary basal doses administered typically with the same infusion pumps. Various devices exist that enable the determination of the appropriate bolus to supplement the basal profiles. For example, prior to the ingestion of a large quantity of carbohydrates, the patient is able to calculate a carbohydrate bolus and administer the same with the infusion pump so that the intake of the carbohydrates does not adversely impact the patient's physiology. Such devices are generally provided with functions that allow the users to enter certain parameters suitable or necessary for the bolus or insulin dosage calculation amount, and perform the actual calculation based on one or more of the entered parameters to derive at the appropriate bolus dosage amount.

The present disclosure allows a user to intentionally under dose an insulin bolus amount as a safety margin against a hypoglycemic event occurring. Once an initial insulin dose has started to take effect, a subsequent measurement of the user's blood glucose level and rate of change may be taken. Based upon the subsequent measurement, more insulin may be administered to fine tune the user's blood glucose level. In particular, the present disclosure helps avoid the long-term health risks of high blood glucose levels that typically result from patients under dosing.

FIG. 1 shows a data monitoring and management system such as, for example, an analyte (e.g., glucose) monitoring system in accordance with some embodiments of the present disclosure. Note that the present disclosure is frequently described herein with reference to diabetes treatment based on measurement and control of glucose levels using insulin, however, the present disclosure is applicable to treatment of many different diseases based on measurement and/or control of many different analytes using many different medications. As depicted in FIG. 1, an analyte monitoring system 100 may include a sensor 101, a data processing unit (e.g., sensor electronics) 102 connectable to the sensor 101, and a receiver unit 104 which is configured to communicate with the data processing unit 102 via a communication link 103. In some embodiments of the present disclosure, the sensor 101 and the data processing unit (e.g., sensor electronics) 102 may be configured as a single integrated assembly 110. In certain embodiments, the single integrated assembly 110 that includes sensor and sensor electronics may be configured as an on-body patch device. In such embodiments, the on-body patch device may be configured for, for example, radio frequency identification (RFID) or radio frequency (RF) communication with a reader device/receiver unit 104, and/or an insulin pump.

In certain embodiments, the receiver unit 104 may be further configured to transmit data to a data processing terminal 105 to evaluate or otherwise process or format data received by the receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the receiver unit 104, the data processing terminal 105.

Only one sensor 101, data processing unit 102, and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105.

The analyte monitoring system 100 may be a continuous monitoring system, or semi-continuous, or a discrete monitoring system. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in or on the body of a user whose analyte level is being monitored. The data processing unit 102 is coupleable to the sensor 101 so that both devices are positioned in or on the user's body, with at least a portion of the analyte sensor 101 positioned transcutaneously. The data processing unit 102 in certain embodiments may include a portion of the sensor 101 (proximal section of the sensor in electrical communication with the data processing unit 102) which is encapsulated within or on the printed circuit board of the data processing unit 102 with, for example, potting material or other protective material. The data processing unit 102 performs data processing functions, where such functions may include but are not limited to, filtering and encoding of data signals, each of which corresponds to a sampled analyte level of the user, for transmission to the receiver unit 104 via the communication link 103. In some embodiments, the sensor 101 or the data processing unit 102 or a combined sensor/data processing unit may be wholly implantable under the skin layer of the user.

In one aspect, the receiver unit 104 may include an analog interface section including an RF receiver and an antenna that is configured to communicate with the data processing unit 102 via the communication link 103, and a data processing section for processing the received data from the data processing unit 102 such as data decoding, error detection and correction, data clock generation, and/or data bit recovery.

Referring still to FIG. 1, the data processing terminal 105 may include an infusion device such as an insulin infusion pump or the like, which may be configured to administer insulin to patients, and which may be configured to communicate with the receiver unit 104 for receiving, among others, the measured analyte level. Alternatively, the receiver unit 104 may be configured to integrate an infusion device therein so that the receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user). An insulin bolus calculator may be operatively coupled to the receiver unit 104 to determine an insulin dose that is required based upon the analyte data received from the sensor device/electronics.

In particular embodiments, the data processing terminal 105, which may include an insulin pump, may be configured to receive the analyte signals from the data processing unit 102, and thus, incorporate the functions of the receiver unit 104 including data processing for managing the patient's insulin therapy and analyte monitoring.

Figure 2:
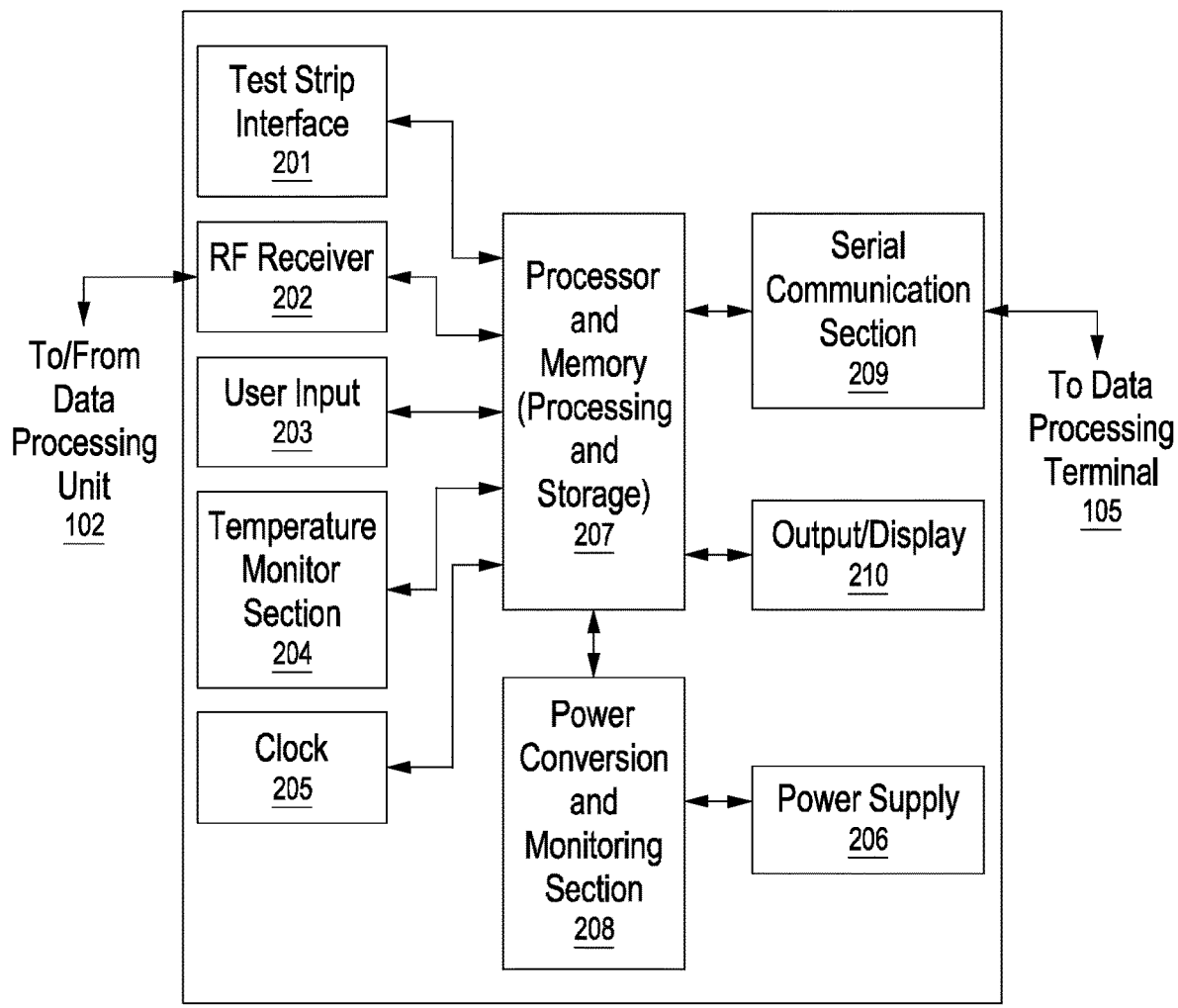
FIG. 2 is a block diagram of a receiver/monitor unit such as that shown in FIG. 1 in accordance with some embodiments of the present disclosure.

FIG. 2 is a block diagram of a receiver/monitor unit or insulin pump such as that shown in FIG. 1 in accordance with certain embodiments. The receiver unit 104 (FIG. 1) may include one or more of a blood glucose test strip interface 201, an RF receiver 202, an input 203, a temperature monitor section 204, and a clock 205, each of which is operatively coupled to a processing and storage section 207. In certain embodiments, a receiver unit, such as receiver unit 104, also includes a power supply 206 operatively coupled to a power conversion and monitoring section 208. Further, the power conversion and monitoring section 208 is also coupled to the receiver processor 207. Moreover, also shown are a receiver serial communication section 209, and an output 210, each operatively coupled to the processing and storage unit 207. The receiver may include user input and/or interface components or may be free of user input and/or interface components.

In one aspect, the RF receiver 202 is configured to communicate, via the communication link 103 (FIG. 1) with the data processing unit (sensor electronics) 102, to receive encoded data from the data processing unit 102 for, among others, signal mixing, demodulation, and other data processing. The input 203 of the receiver unit 104 is configured to allow the user to enter information into the receiver unit 104 as needed. In one aspect, the input 203 may include keys of a keypad, a touch-sensitive screen, and/or a voice-activated input command unit, and the like. The temperature monitor section 204 may be configured to provide temperature information of the receiver unit 104 to the processing and storage section 207, while the clock 205 provides, among others, real time or clock information to the processing and storage section 207.

Each of the various components of the receiver unit 104 shown in FIG. 2 is powered by the power supply 206 (or other power supply) which, in certain embodiments, includes a battery. The output/display 210 of the receiver unit 104 is configured to provide, among others, a graphical user interface (GUI), and may include a liquid crystal display (LCD) for displaying information and/or allowing a user to enter information. The receiver unit 104 may also include a storage section such as a programmable, non-volatile memory device as part of the processor 207, or provided separately in the receiver unit 104, operatively coupled to the processor 207.

As previously mentioned, conventional treatment of diabetes includes the reliance on medication, such as insulin, by some diabetic individuals to help regulate their blood glucose. Insulin dependent multiple daily injectors (MDI) typically measure their blood glucose (e.g., using a blood glucose meter or in vivo analyte sensor) prior to the administration of insulin to determine the correct insulin dose required. If an MDI is preparing to eat a meal, the insulin dose calculation also accounts for the number of grams of carbohydrates that the MDI estimates will be consumed in the meal. The accuracy of the calculated insulin dose depends on certain dynamic factors, such as how much insulin remains in a user's blood stream from a prior insulin dose (hereinafter referred to as "insulin on-board"). The MDI has visibility to some of the factors, but are blind to others. Thus, conventional insulin dosing may be characterized as an open loop control model, in which the MDI measures his or her blood glucose level and injects insulin one time. According to embodiments of the present disclosure, insulin dosing may be performed using a closed loop model in which a glucose monitoring system including an insulin pump automatically determines and administers medication to the user based on analyte data acquired by the system. Still further, insulin dosing can be performed using a semi-closed loop model, in which a glucose monitoring system determines the amount of insulin required and prompts the user to inject the insulin dose. Equation 1, seen below, illustrates a relationship to determine an insulin bolus dose amount that can be calculated by either a user or by a glucose monitoring system.

$$insulin\,dose = \frac{BG - \text{target}}{insulinfactor} + \frac{carbs}{carbfactor} - iob \quad \text{(Equation 1)}$$

In the above relationship, BG represents a blood glucose level that may be measured using, e.g., a test strip and/or a continuous glucose sensing device. The target is the desired glucose level after the administration of the calculated insulin dose. The time period at which the target glucose level is reached after the administration of the insulin dose is related to the user's "insulin action time." Typically, a user's insulin action time is estimated between 2 and 6 hours. In addition, a healthcare provider can help estimate a user's insulin action time by plotting a graph of a user's blood glucose profile with respect to time after an insulin injection. The insulin sensitivity factor (insulinfactor) is the amount, in mg/dL, that the blood glucose level may be lowered using 1 unit of insulin. Moreover, the insulin sensitivity factor may be user specific, but is typically around 10 mg/dL/U.

A user specific insulin sensitivity factor may be determined using the "1500 Rule" for individuals who use short-acting insulin. For example, the 1500 Rule estimates the point drop in mg/dL for every unit of short acting insulin taken. Using the "1500 Rule" the insulin sensitivity factor may be determined by dividing 1500 by the total daily dose of short-acting insulin. Alternately, for individuals that use fast-acting insulin, the "1800 Rule" may be applied to determine an insulin sensitivity factor. For example, 1800 Rule estimates the point drop in mg/dL for each unit of rapid-acting insulin taken. To determine an insulin sensitivity factor using the "1800 Rule", 1800 is divided by a user's total daily dose of fast-acting insulin. Other methods of determining a user's insulin sensitivity factor are also contemplated.

The carbohydrate factor (carbfactor) represents the amount, in grams, of carbohydrates that may be disposed of by 1 unit of insulin, and typically is around 15 grams/U for fast-acting insulin. Moreover, an estimate of the carbohydrates consumed at mealtime (carbs) can also be used in insulin bolus determination. In further embodiments, the data processing unit 102 and/or the receiver unit 104, and/or the data processing terminal/infusion section 105 may be configured to determine various insulin dose calculations, for example, as described in greater detail in the embodiments below.

With reference to Table 1, assuming an initial BG of 200 mg/dL, a target blood glucose level of 100 mg/dL a carbohydrate consumption of 50 grams, and 0 units of insulin on-board, the present methods, apparatuses, and/or systems can determine an insulin dose of 13.3 units as calculated using Equation 1.

TABLE 1

Blood Glucose Correction Using Insulin Bolus Dose

| Time (hour) | Glucose Level (mg/dL) | User Carbohydrate Estimation (grams) | Insulin On-Board (Units) | Insulin Dose (Units) | System Calculation (Units) |
|---|---|---|---|---|---|
| 0 | 200 | 50 | 0.0 | 13.3 | $=\frac{(200-100)}{10}+\frac{50}{15}-0$ |
| 1 | 200 | | 10.0 | | |
| 2 | 167 | | 6.7 | | |
| 3 | 133 | | 3.3 | | |
| 4 | 100 | | 0.0 | | |

Figure 3:
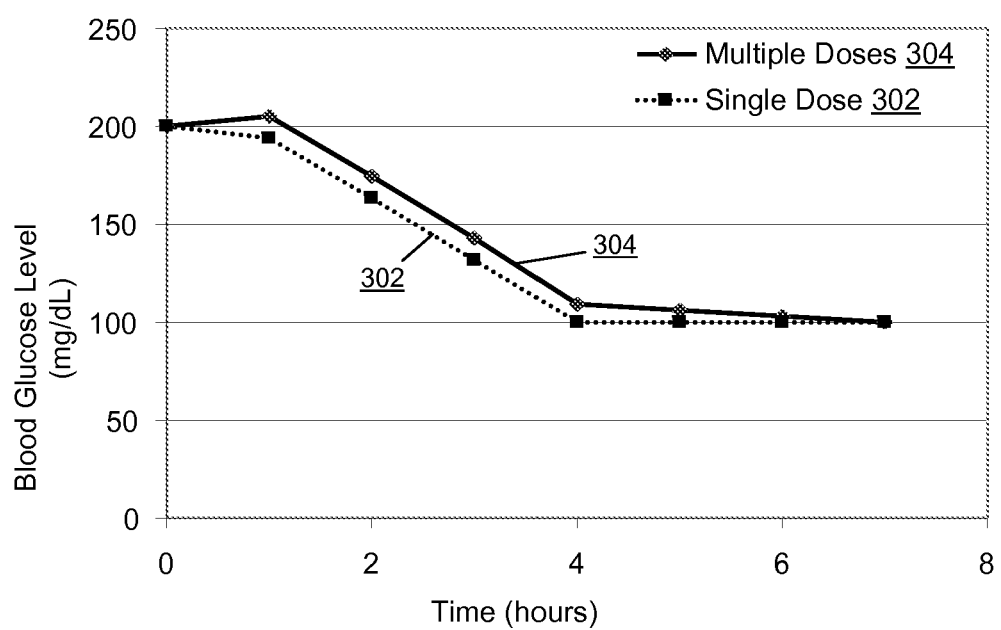
FIG. 3 is a graph of the analyte level of a user regulated using a single medication dose compared to the analyte level of a user regulated with multiple medication doses in accordance with some embodiments of the present disclosure.

As a safety margin against hypoglycemia, some MDIs may intentionally under dose insulin so that their blood glucose stays at a higher level for a longer period of time. The present disclosure allows the user to go from open loop control to closed loop control. For example, a user can intentionally under dose an insulin bolus amount, and once that insulin dose has started to take effect, a subsequent measurement of the user's blood glucose level may be taken, and based upon the subsequent measurement, more insulin may be administered to fine-tune the user's blood glucose level. The subsequent blood glucose measurement may be taken, e.g., using a blood glucose meter and/or a continuous glucose monitoring device. FIG. 3 graphically illustrates a user's blood glucose level over time using a traditional single insulin dose 302, and the blood glucose level using a safer, two insulin dose approach 304 according to the present disclosure. As seen in FIG. 3, the blood glucose level using a single insulin dose approach 302 reaches the 100 mg/dL level in four hours. Using the safer two insulin dose approach 304, the user is not likely to be below the target blood glucose level at 4 hours. The value above target glucose level, combined with the second insulin dose helps better manage the risk of hypoglycemia.

Table 2 below illustrates various embodiments contemplated by the present disclosure that may be used to determine an initial or first insulin bolus dose.

TABLE 2

Examples to Determine first Insulin Dose Amount

| Approaches: | Initial Dose (Units) |
|---|---|
| 1. Traditional | 13.3 |
| 2. Initial target is 20 mg/dL higher | 11.3 |
| 3. Target follow up dose size 2.5 U | 10.8 |
| 4. Percentage of total dose, 80% | 10.6 |
| 5. Percentage of carbohydrate, 70% | 12.3 |
| 6. Percentage of correction, 70% | 10.3 |

The various approaches described herein may be performed by the data processing unit 102, the receiver unit 104, and/or the data processing terminal/infusion section 105 of FIG. 1. A second insulin dose may be determined in a similar manner, using the individual's current blood glucose value, zero grams of carbohydrates, and subtracting the insulin on-board remaining from the first dose. Approach 1 is a single insulin dose calculation as described above with reference to Table 1. Approaches 2-6 apply to a multiple (for example, two or more) insulin dose method, which includes a determination of a first insulin dose that is smaller than the insulin dose that would be determined using Approach 1, and a determination of a second or more insulin doses that may be administered at a later time.

Approach 2 determines the first insulin dose using Equation 1 but using a target analyte level that is, e.g., 20 mg/dL higher than the actual target analyte level. To determine the second insulin dose amount using Approach 2, the receiver unit 104 for example, may be configured to determine an insulin dose using Equation 1 with the normal target analyte level, using the user's blood glucose level obtained at the time of the second dose calculation, and subtracting the insulin on-board remaining from the first insulin dose.

Approach 3 targets the second insulin dose at 2.5 units, so the receiver unit 104 may be configured to subtract 2.5 units from the determined insulin dose amount from Equation 1 in determining the first insulin dose amount. To determine the second insulin dose amount using Approach 3 the receiver unit 104 for example, may be configured to determine an insulin dose using Equation 1 using the user's blood glucose level obtained at the time of the second dose calculation, and subtracting the insulin on-board remaining from the first insulin dose.

Using Approach 4, the receiver unit 104 may be configured to determine an insulin dose using Equation 1, and then determining 80% of that value as the first insulin dose. To determine the second insulin dose amount using Approach 4 the receiver unit 104 may be configured to determine an insulin dose using Equation 1 using the user's blood glucose level obtained at the time of the second dose calculation, and subtracting the insulin on-board remaining from the first insulin dose.

To determine the first insulin dose using Approach 5, the receiver unit 104 may be configured to determine an insulin dose using Equation 1 but only using 70% of the estimated carbohydrate consumption in the determination. To determine the second insulin dose amount using Approach 5, the receiver unit 104 may be configured to determine an insulin dose using Equation 1 using the user's blood glucose level determined at the time of the second dose calculation, with zero grams carbohydrates, and subtracting the insulin on-board remaining from the first insulin dose.

To determine the first insulin dose using Approach 6, the receiver unit 104 can calculate an insulin dose using Equation 1 but only using 70% of the correction term $$\left(\text{i.e., } \frac{BG - \text{target}}{\text{insulinfactor}}\right)$$

in the calculation. To calculate the second insulin dose amount using Approach 6, the receiver unit 104 may be configured to determine an insulin dose using Equation 1 using the user's blood glucose level at the time of the second dose calculation, with zero grams carbohydrates, and subtracting the insulin on-board remaining from the first insulin dose.

By way of an example, Table 3 below illustrates the potential danger of a user entering incorrect carbohydrate consumption data into the receiver unit 104 by estimating 50 grams but only consuming 35 grams in determining an insulin bolus dose. Specifically, in the present example, the user is calculating an insulin bolus dose with a target analyte level of 120 mg/dL.

TABLE 3

Overestimated Carbohydrate Consumption and Single Insulin Dose

| Time (hour) | Analyte Level (mg/dL) | User Carbohydrate Estimation (grams) | User Carbohydrate Actual (grams) | Insulin On-Board (Units) | User's Insulin Calculation (Units) | System Calculation (Units) |
|---|---|---|---|---|---|---|
| 0 | 200 | 50 | 35 | 0.0 | 11.3 | $= \frac{(200 - 120)}{10} + \frac{50}{15} - 0$ |
| 1 | 190 | | | | 10.0 | |
| 2 | 157 | | | | 6.7 | |
| 3 | 123 | | | | 3.3 | |
| 4 | 90 | | | | 0.0 | |

However, because the user overestimates the carbohydrate consumption, the subsequent insulin dose calculation is also overestimated. This results in a lower than target blood glucose level of 90 mg/dL four hours after the consumption of the meal. In this example, the insulin on-board represents the amount of insulin in the user's system that remains from the insulin dose.

Table 4 below illustrates the same example as above but with a follow up insulin bolus dose that is administered 3 hours after mealtime. Again, the initial insulin dose is calculated with a target of 120 mg/dL, and the user miscalculates the carbohydrate consumption by estimating 50 grams but only consuming 35 grams in determining an insulin bolus dose. However, rather than administering the entire 12.3 units of insulin determined from the calculation, the user under doses with 11.3 units, based upon the calculation of the first insulin dose by the receiver unit 104, and then follows up with an additional 1 unit dose at hour 3.

TABLE 4

Miscalculated Carbohydrate Consumption and Two Insulin Doses

| Time (hour) | Sensor Analyte Level (mg/dL) | User Carbohydrate Estimation (grams) | User Carbohydrate Actual (grams) | Insulin On-Board (Units) | User's Insulin Calculation (Units) | System Calculation (Units) |
|---|---|---|---|---|---|---|
| 0 | 200 | 50 | 35 | 0.0 | 11.3 | $= \frac{(200 - 120)}{10} + \frac{50}{15} - 0$ |
| 1 | 195 | | | | 8.5 | |

TABLE 4-continued

Miscalculated Carbohydrate Consumption and Two Insulin Doses

| Time (hour) | Sensor Analyte Level (mg/dL) | User Carbohydrate Estimation (grams) | User Carbohydrate Actual (grams) | Insulin On-Board (Units) | User's Insulin Calculation (Units) | System Calculation (Units) |
|---|---|---|---|---|---|---|
| 2 | 167 | | | 5.7 | | |
| 3 | 138 | | | 2.8 | 1.0 | $= \frac{(138-100)}{10} + \frac{0}{15} - 2.8$ |
| 4 | 108 | | | 0.8 | | |
| 5 | 105 | | | 0.5 | | |
| 6 | 103 | | | 0.3 | | |
| 7 | 100 | | | 0.0 | | |

In this example, although the user overestimates the carbohydrate consumption for entry into the receiver unit 104 to calculate an insulin bolus dose, because the user changes the target, and a second insulin dose of 1 unit at hour 3, the user's blood analyte level is still at 100 mg/dL 7 hours after meal time.

Figure 4:
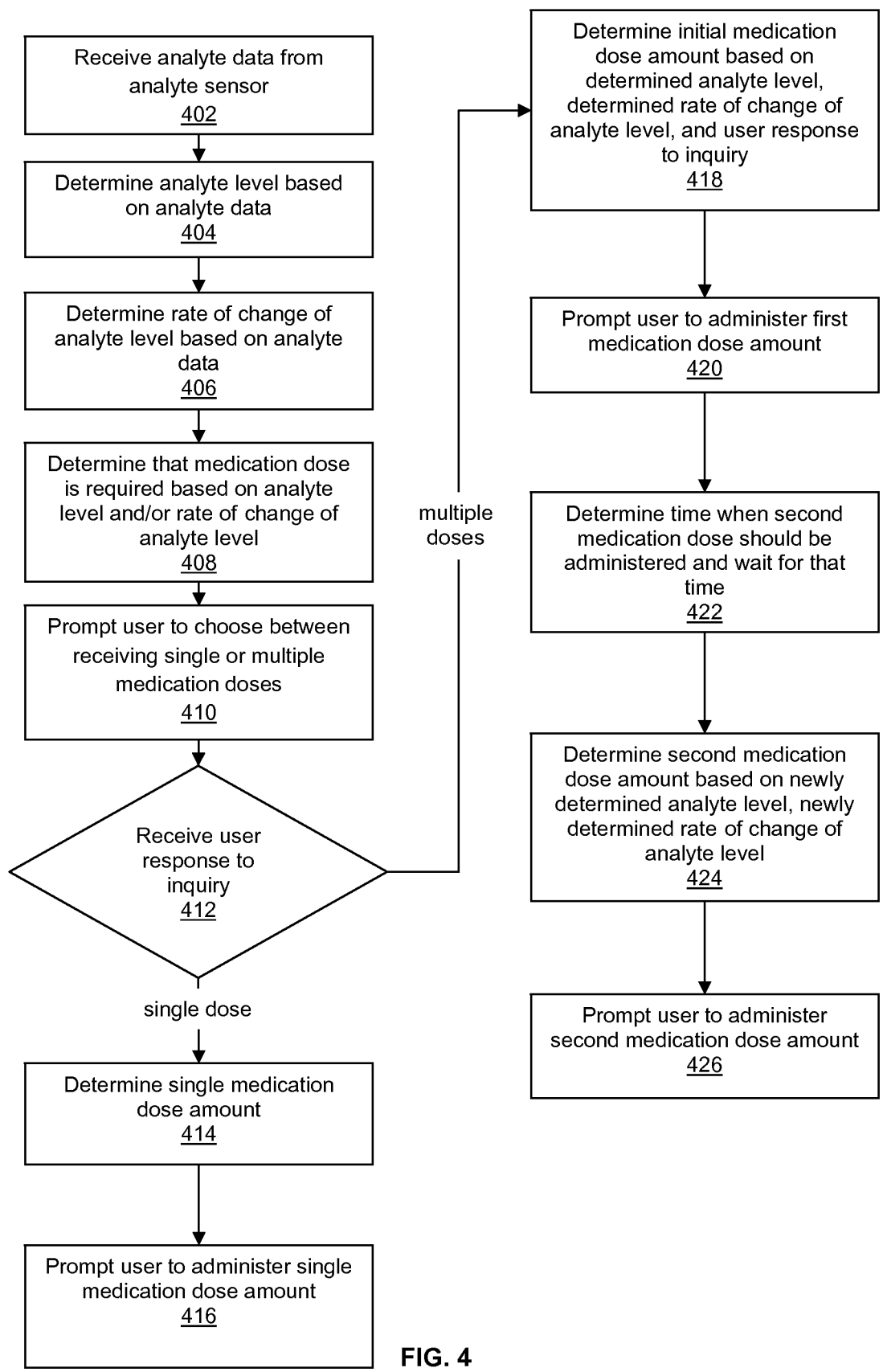
FIG. 4 is a flow chart illustrating an example method for determining a first and second medication dose amount in accordance with some embodiments of the present disclosure.

FIG. 4 is a flow chart illustrating an example method for determining multiple insulin dose amounts to safeguard against hypoglycemia in certain embodiments. Referring to FIG. 4, in some embodiments, the receiver unit 104 of FIG. 1 may be configured to receive analyte data related to an analyte level of a user from an analyte sensor device (402). The analyte data may be received via wired or wireless transmission from a sensor assembly 110 worn on the body of the user. The receiver unit 104 can include a portable analyte meter, a laptop computer, a smart phone, a personal computer, a personal digital assistant, etc. Moreover, the receiver unit 104 may be a user device, a parental device, and/or a healthcare provider device.

The analyte level of the user may be determined based on the analyte data (404) received at a processor 207 of FIG. 2, of the receiver unit 104, for example. The analyte level of the user may be determined directly upon receipt of the analyte data, or the receiver unit 104 can wait to determine the analyte level until a predetermined time. In addition, the rate of change of the analyte level of the user may be determined based on the received analyte data (406). Based upon at least one of the determined analyte level and the determined rate of change of the analyte level, a determination may be made, e.g., by the processor 207, if a medication dose should be administered to the user (408). For example, the processor 207 can apply a heuristic algorithm to the analyte data to determine the confidence in projecting the response of the blood analyte level to a meal and insulin injection. By way of example, the medication dose may be an insulin dose. The insulin dose may be administered via oral medication, a syringe, and/or an insulin pen to name a few. In addition, insulin may be automatically administered via an insulin pump operatively coupled to the infusion section 105.

The receiver unit 104 can prompt the user to choose between receiving one or multiple doses of the medication (410). The receiver unit 104 can divide the insulin dose calculation into multiple portions, and the prompt may be presented to the user via at least one of a textual message displayed on an output display 210 of the receiver unit 104, a vibratory alert, an audible message, and/or a vibratory alert to name a few. By way of example, the user can respond to the prompt by one or more of entering a response using a user input touch screen 203 that is operatively coupled to the receiver unit 104, entering a response using a user input keypad 203 operatively coupled to the receiver unit 104, and/or providing a voice command that is recognized, e.g., by input unit 203 operatively coupled to the receiver unit 104. The user's response to the prompt may be received (412) by the receiver unit 104. If the user response indicates that only one medication dose is to be administered, the receiver unit 104 determines a single medication dose amount based upon at least one of the determined analyte level and/or the determined analyte rate of change (414), and the receiver unit 104 can prompt the user to administer a single medication dose amount (416). Alternately, the receiver unit 104 can prompt the infusion section 105 to administer the single medication dose amount.

However, if the user's response to the prompt indicates that the user would like to receive multiple medication doses, the receiver unit 104 can determine and/or calculate a first medication dose amount that is based upon at least one of the determined analyte level, the determined analyte rate of change, and/or the received user response (418). The first medication dose may be a maximum dose that the receiver unit 104 determines will not unduly risk hypoglycemia in the user. The receiver unit 104 can prompt the user and/or an insulin infusion device 105 to administer the first medication dose (420). The prompt may be presented to the user in the form of a textual message displayed on a display screen 210 of the receiver unit 104, a vibratory alert, an audible message, and/or a vibratory alert to name a few. The processor 207 can apply a heuristic algorithm to the analyte data to determine an optimal time for the first medication dose to be administered. Factors that can affect this time, and which may be taken into consideration by the heuristic algorithm, can include the user's insulin reaction time, the user's carbohydrate reaction time, the user's blood analyte, rate of change of the analyte level, and acceleration of the analyte level. In some embodiments, the receiver unit 104 can prompt the user and/or the insulin infusion device 105 to administer the first medication dose immediately, or at a later time. When the recommended time arrives, the user can postpone or shut off the recommendation from the receiver unit 104. The time that the receiver unit 104 recommends to the user may be modified to account for user behavior and experience. For example, the user may be alerted several minutes prior to the recommended time to allow for the user's reaction time.

A second time when a second medication dose amount should be administered can also be determined (422) by the receiver unit 104. The receiver unit 104 can determine and/or calculate the second medication dose amount based upon a newly determined analyte level, a newly determined analyte rate of change (424). The second medication dose may be a smaller or larger medication dose than the first, or an equal amount. In some embodiments, the second medication dose amount may be determined and/or calculated based on the latest analyte data, a combination of current and prior analyte data, and/or a prediction of a future analyte level. The determination of the second medication dose amount can include comparing the user's blood analyte to a model or threshold value to determine the reaction to the first medication dose amount, and/or traditional medication dosing factors such as the updated blood analyte information, insulin on-board, carbohydrate input, and the user's reaction times, to name a few.

The receiver unit 104 can prompt the user to administer the second medication dose amount (426). The prompt may be presented to the user in the form of a textual message displayed on a display screen of the receiver unit 104, a vibratory alert, an audible message, and/or a vibratory alert to name a few. The receiver unit 104 can apply a heuristic algorithm to the analyte data to determine an optimal time for the second medication dose. Factors that can affect this time, and which may be taken into consideration by the heuristic algorithm, can include the user's insulin reaction time, the user's carbohydrate reaction time, the user's blood analyte, rate of change of the analyte level, and acceleration of the analyte level.

As described, the user may be prompted to administer the second medication after the first medication dose is administered. In some embodiments, when the second time arrives, the user can postpone or shut off the prompt from the receiver unit 104. The first and/or second time that the receiver unit 104 prompts the user to administer the first and/or second medication dose may be modified to account for user behavior and experience. For example, the user may be alerted several minutes prior to the first and/or second time to allow for the user's reaction time. Although the example illustrated in FIG. 4 describes calculating and administering two medication doses, it will be understood that more than two medication doses may be determined and user prompted for administration in accordance with the present methods, apparatuses, and systems of the invention. The present methods, apparatuses, and systems can just as easily be used by insulin pump users. In such an instance, the medication doses may be administered as a bolus using the insulin infusion section 105, and insulin infusion section 105 may be prompted to administer the determined medication doses.

Figure 5:
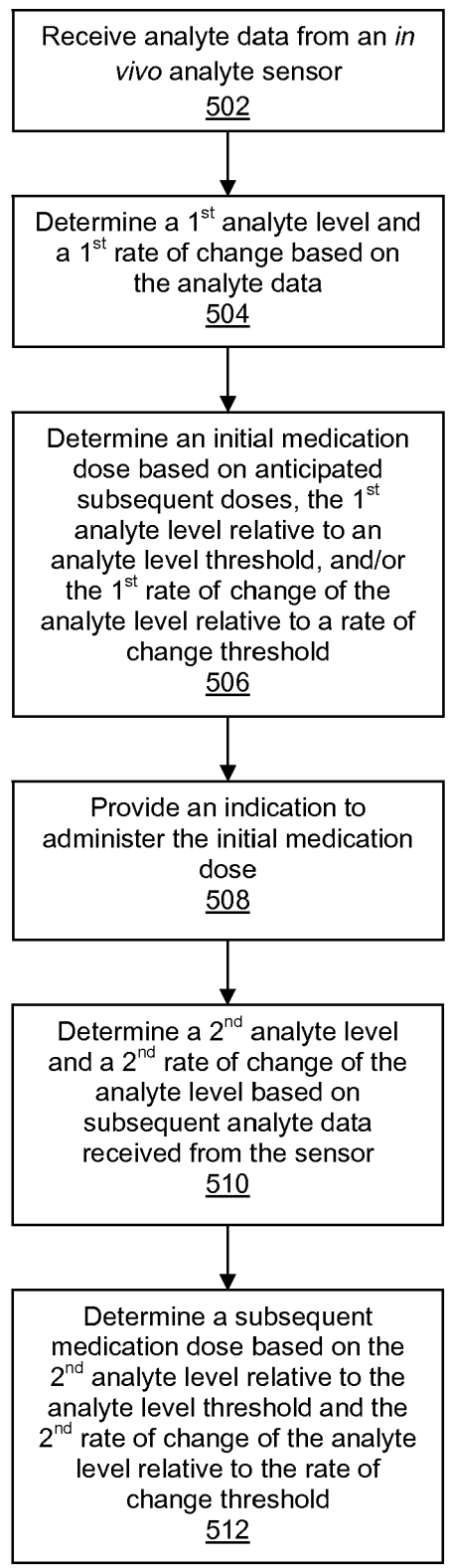
FIG. 5 is a flow chart illustrating an example method of optimizing medication dosages in accordance with some embodiments of the present disclosure.

FIG. 5 is a flow chart illustrating an example method of optimizing medication dosages according to embodiments of the present disclosure. Referring to FIG. 5, in some embodiments, the receiver unit 104 may be configured to receive analyte data related to an analyte level from an analyte sensor positioned through a skin layer of a user (502). The analyte data may be received via wired or wireless transmission from a sensor assembly 110 worn on the body of the user. The receiver unit 104 can include a portable analyte meter, a laptop computer, a smart phone, a personal computer, a personal digital assistant, etc. Moreover, the receiver unit 104 may be a user device, a parental device, and/or a healthcare provider device.

A first analyte level and a first analyte rate of change may be determined (504) based on the analyte data received at a processor 207 of the receiver unit 104, for example. The first analyte level and/or first analyte rate of change may be determined directly upon receipt of the analyte data, or the receiver unit 104 can wait to determine the analyte level until a predetermined time. Based upon anticipating the more than one dose will be administered, a comparison of the first analyte level to a threshold analyte level, and a comparison of the first rate of change of the analyte level to a threshold rate of change, a determination may be made, e.g., by the processor 207, of an appropriate medication dose (506). For example, the processor 207 can apply a heuristic algorithm to the analyte data to determine the confidence in projecting the response of the analyte level to a meal and a medication injection. By way of example, the medication may be an insulin dose. The insulin dose may be administered via oral medication, a syringe, and/or an insulin pen to name a few. In addition, insulin may be automatically administered via an insulin pump operatively coupled to the infusion section 105. Thus, the receiver unit 104 can calculate the initial medication dose to be administered. Additionally, in some embodiments, the processor 207 of the receiver 104 unit can predict the likelihood of a hypoglycemic event occurring if the calculated medication dose is administered as a single dose. If the processor 207 predicts that a hypoglycemic event is likely to occur if the medication dose is administered as a single dose, then the receiver unit 104 can determine that the calculated medication dose should be administered as two discrete doses.

The determination to administer the calculated medication dose can also be in response to an affirmative selection of a decision at a user interface 210 operatively coupled to the receiver unit 104. For example, the receiver unit 104 can select a calculation method to calculate doses based on at least one of the analyte level, the analyte rate of change, and the prediction of the hypoglycemic event. More specifically, one or more of the doses can be calculated using a selection of one or more of the approaches detailed in Table 2 above.

In some embodiments, the receiver unit 104 and/or insulin infusion section 105 can administer, automatically and/or in response to an input at the user interface 210, the initial medication dose without human intervention or merely provide an indication to the user to administer the initial medication dose (508). The receiver unit 104 can apply a heuristic algorithm to the analyte data to determine an optimal time to administer the initial dose. Factors that can affect this time, and which may be taken into consideration by the heuristic algorithm, can include the user's insulin reaction time, the user's carbohydrate reaction time, the user's blood analyte, rate of change of the analyte level, and acceleration of the analyte level.

Based on subsequent data received from the analyte sensor, the processor 207 of the receiver unit 104 can determine a second analyte level and a second rate of change of the analyte level (510). As described above, a subsequent medication dose can be determined based upon the second analyte level and the second rate of change of the analyte level (512). In some embodiments, determining the subsequent medication dose includes determining a time at which to administer the subsequent medication dose as described above. As with the initial dose, a user interface of the receiver unit 104 may provide a prompt to the user to administer the subsequent dose. In some embodiments, the insulin infusion section 105 can administer the subsequent medication dose and may request that the user confirm that the dose should be administered. As noted above, the subsequent dose may be calculated based at least in part on an updated determination of the analyte level and the analyte rate of change relative to the threshold level and threshold rate of change.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

The invention claimed is:

1. An apparatus comprising:
a processor in electrical communication with an in vivo sensor; and
memory coupled to the processor and operative to store instructions executable by the processor, the instructions comprising:
determining to administer medication based on at least one of a first analyte level and a first rate of change of the analyte level determined from analyte data received from the in vivo sensor;
calculating, based on a determination to administer the medication as more than one discrete medication dose instead of a single medication dose, a first discrete medication dose based on the first analyte level relative to an analyte level threshold, the first rate of change of the analyte level relative to a rate of change threshold, and an anticipated administration of at least one subsequent discrete medication dose; and
at a predetermined period of time following calculation of the first discrete medication dose, calculating the at least one subsequent discrete medication dose based on both of a second analyte level determined from subsequent analyte data received from the in vivo sensor relative to the analyte level threshold and a second rate of change of the analyte level determined from the subsequent analyte data received from the in vivo sensor relative to the rate of change threshold.

2. The apparatus of claim 1, wherein the analyte level threshold is a target analyte level.

3. The apparatus of claim 2, wherein the target analyte level is a target glucose level.

4. The apparatus of claim 3, wherein the target glucose level is 120 mg/dl.

5. The apparatus of claim 2, wherein the first discrete medication dose is lower than the dose that would be necessary to achieve the target analyte level in the absence of the at least one subsequent discrete medication dose.

6. The apparatus of claim 1, wherein the first analyte level and the second analyte level are glucose levels.

7. The apparatus of claim 1, wherein the instructions further include providing an indication to administer at least one of the first discrete medication dose or the at least one subsequent medication dose.

8. The apparatus of claim 1, wherein the instructions further include providing an indication to administer at least one of the first discrete medication dose and the at least one subsequent discrete medication dose further by transmitting signals to an automated medication delivery device.

9. The apparatus of claim 1, wherein the first discrete medication dose and the at least one subsequent discrete medication dose are insulin doses.

10. The apparatus of claim 1, wherein the apparatus is a continuous monitoring device receiver unit or a medication delivery device receiver unit.

11. The apparatus of claim 1, wherein the first discrete medication dose is lower than if calculated based on a determination to administer the medication as a single medication dose.

12. A method comprising:
monitoring continuously an analyte level by an in vivo sensor;
determining to administer medication based on at least one of a first analyte level and a first rate of change of the analyte level determined from analyte data received from the in vivo sensor;
based on a determination to administer the medication as more than one discrete medication dose instead of a single medication dose, calculating, using a processor in electrical communication with the in vivo sensor and memory coupled to the processor, a first discrete medication dose based on the first analyte level relative to an analyte level threshold, the first rate of change of the analyte level relative to a rate of change threshold, and an anticipated administration of at least one subsequent discrete medication dose; and
at a predetermined period of time following calculation of the first discrete medication dose, calculating, using the processor and memory, the at least one subsequent discrete medication dose based on both of a second analyte level determined from subsequent analyte data received from the in vivo sensor relative to the analyte level threshold and a second rate of change of the analyte level determined from the subsequent analyte data received from the in vivo sensor relative to the rate of change threshold.

13. The method of claim 12, wherein the analyte level threshold is a target analyte level.

14. The method of claim 13, wherein the target analyte level is a target glucose level.

15. The method of claim 14, wherein the target glucose level is 120 mg/dl.

16. The method of claim 13, wherein the first discrete medication dose is lower than the dose that would be necessary to achieve the target analyte level in the absence of the at least one subsequent discrete medication dose.

17. The method of claim 12, wherein the first analyte level and the second analyte level are glucose levels.

18. The method of claim 12, further comprising providing an indication to administer one or both of the first discrete medication dose and the at least one subsequent discrete medication dose.

19. The method of claim 12, further comprising providing an indication to administer at least one of the first discrete medication dose and the at least one subsequent discrete medication dose further by transmitting signals from the in vivo sensor to an automated medication delivery device.

20. The method of claim 12, wherein the first discrete medication dose and the at least one subsequent discrete medication dose are insulin doses.

21. The method of claim 12, wherein the first discrete medication dose is lower than if calculated based on a determination to administer the medication as a single medication dose.

* * * * *